United States Patent
Xu et al.

(10) Patent No.: US 10,238,273 B2
(45) Date of Patent: Mar. 26, 2019

(54) ENDOSCOPIC FLUID CONTROL VALVE AND ENDOSCOPE THEREOF

(71) Applicant: SonoScape Co., Shenzhen (CN)

(72) Inventors: Keduan Xu, Shenzhen (CN); Gong'an Wu, Shenzhen (CN)

(73) Assignee: SONOSCAPE MEDICAL CORP., Shenzhen, Guangdong (CN)

( * ) Notice: Subject to any disclaimer, the term of this patent is extended or adjusted under 35 U.S.C. 154(b) by 110 days.

(21) Appl. No.: 14/896,833

(22) PCT Filed: Jun. 4, 2014

(86) PCT No.: PCT/CN2014/079142
§ 371 (c)(1),
(2) Date: Dec. 8, 2015

(87) PCT Pub. No.: WO2014/194821
PCT Pub. Date: Dec. 11, 2014

(65) Prior Publication Data
US 2016/0143516 A1    May 26, 2016

(30) Foreign Application Priority Data
Jun. 8, 2013 (CN) .......................... 2013 1 0228237

(51) Int. Cl.
*A61B 1/015* (2006.01)
*A61B 1/00* (2006.01)

(52) U.S. Cl.
CPC .......... *A61B 1/015* (2013.01); *A61B 1/00068* (2013.01)

(58) Field of Classification Search
CPC .......................... A61B 1/015; A61B 1/00068
See application file for complete search history.

(56) References Cited

U.S. PATENT DOCUMENTS

| 5,840,016 A | * | 11/1998 | Kitano | A61B 1/12 251/335.2 |
| 6,346,075 B1 | | 2/2002 | Arai et al. | |
| 2006/0266423 A1 | * | 11/2006 | Akiba | A61B 1/015 137/565.01 |
| 2010/0087705 A1 | * | 4/2010 | Byers | A61B 1/00128 600/104 |
| 2010/0317922 A1 | * | 12/2010 | Kumai | A61B 1/00068 600/118 |

(Continued)

FOREIGN PATENT DOCUMENTS

| CN | 201015586 Y | 2/2008 |
| CN | 202335846 U | 7/2012 |
| JP | 7-51222 A | 2/1995 |

(Continued)

*Primary Examiner* — John P Leubecker
*Assistant Examiner* — Genja Frankert
(74) *Attorney, Agent, or Firm* — Hauptman Ham, LLP

(57) ABSTRACT

Embodiments of the present invention provide an endoscopic fluid control valve. By having just one fluid outlet, the structure of the endoscopic fluid control valve is made simpler with interior space saving. There is no need for a one-way check valve at an operational portion of the endoscope to prevent fluid backflow, and this makes it easy to clean. An embodiment includes valve housing, valve stem, valve core, elastic component, button, first seal, second seal, third seal, fourth seal, gas inlet, fluid inlet and fluid outlet.

16 Claims, 5 Drawing Sheets

(56) References Cited

U.S. PATENT DOCUMENTS

2011/0118544 A1* 5/2011 Adams .................. A61B 1/015
600/104
2013/0338442 A1* 12/2013 Anderson .......... A61B 1/00068
600/154

FOREIGN PATENT DOCUMENTS

WO     WO 2012/075131 A1    6/2012
WO      WO 2012075131 A1 *   6/2012         A61B 1/00068

* cited by examiner

ENDOSCOPIC FLUID CONTROL VALVE AND ENDOSCOPE THEREOF

CROSS REFERENCE TO RELATED PATENT APPLICATION

This application is the U.S. national phase application of International application number PCT/CN2014/079142, filed on 4 Jun. 2014, which claims the priority benefit of China Patent Applications No. 201310228237.0, filed on 8 Jun. 2013. The above-identified applications are hereby incorporated by reference in their entirety.

TECHNICAL FIELD

The present disclosure is related to the field of biotechnology and medicine, particularly to an endoscopic fluid control valve in an endoscope.

BACKGROUND

Endoscope systems are widely used for medical diagnosis. To observe organs in a body cavity, an elongated portion of an endoscope system is inserted into the body cavity. Then, according to the need, a treatment instrument may be inserted into an insertion passage to perform various therapeutic treatments. For the cleaning and treatment of a treated portion in the body cavity or for expanding the body cavity to increase a field of view, the endoscope is provided with a gas/liquid supply device that can feed, based on the need, water, medical liquid and/or air into the body cavity.

In the prior art, the gas/liquid supply device of the endoscope is controlled by a fluid control valve disposed on an operation portion of the endoscope. A gas inlet for gas feeding, a liquid inlet for liquid feeding, a gas outlet for gas discharge and a liquid outlet for liquid discharge of the endoscope are all disposed on the liquid control valve, with a button thereon to control the feeding of gas and liquid. Due to the limited space in the insertion tube of the endoscope, liquids and gases into the human body, the same pipeline in the insertion tube is used to feed gas and/or liquid into the human body. The liquid outlet and gas outlet extend from the fluid control valve and into an affected area up front, through a three-way tee into the same pipeline and through the insertion tube of the endoscope.

In order to prevent contamination of the fluid control valve, liquid source or gas source due to backflow of bodily fluids, a one-way check valve is provided at an output of the three-way tee. This is to prevent backflow of bodily fluids to the fluid control valve.

In the structure of the fluid control valve of the aforementioned prior art endoscope, the fluid outlet and the gas outlet of the fluid control valve are separate from each other in addition to the need of the three-way tee and check valve. This results in complicated structure as well as increased hardware cost. Moreover, the check valve may be clogged by impurities and thus requires frequent cleaning. As the check valve is disposed inside the operation portion of the endoscope, the need for opening up the operation portion for cleaning tends to cause inconvenience.

SUMMARY

The present invention provides an endoscopic fluid control valve configured with one gas and liquid outlet (in the rest of the text, "gas and liquid outlet" is used interchangeably as "fluid outlet" )so as to reduce the number of outlet. This simplifies the structure of the endoscopic fluid control valve and saves space. This prevents backflow of liquids and eliminates the need for a check valve along the flow path of fluids, making it easy to clean. Additionally, another objective of the present invention is to provide an endoscope using the endoscopic fluid control valve.

An embodiment of an endoscopic fluid control valve in accordance with the present invention includes the components described below.

Valve housing, valve stem, valve core, elastic component, button, first seal, second seal, third seal, fourth seal, gas inlet, liquid inlet and fluid outlet are included.

The valve housing contains the valve stem, the valve core, the elastic component, the first seal, the second seal, the third seal and the fourth seal therein. The valve housing includes following parts arranged in an order as listed from top to bottom: a thick section with a larger diameter and a thin section with a smaller diameter. The gas inlet, the fluid outlet and the liquid inlet are arranged and on the valve housing in a sequential order from top to bottom, with the gas inlet disposed on the thick section of the valve housing and with the fluid outlet and the liquid inlet disposed on the thin section of the valve housing.

The valve stem includes a first through hole 113 which has an upper end and a lower end. The upper end of the first through hole is connected to the button. The lower end of the first through hole includes a vertical section connected to an upper end of the valve core. The lower end of the first through hole also includes a horizontal section traversing through the valve stem. The horizontal section is disposed height-wise between the gas inlet and the fluid outlet.

The valve core is contained within the valve stem and includes a lower end and the upper end. The lower end of the valve core is connected to an upper end of the elastic component. The upper end of the valve core detachably forms an airtight connection with the lower end of the first through hole. The elastic component is contained within the valve stem and includes the upper end and a lower end. The upper end of the elastic component is elastically connected to the lower end of the valve core. The lower end of the elastic component is connected to a bottom end of the valve stem.

The button is disposed at a top portion of the endoscopic fluid control valve and is connected to the vertical section of the first through hole. The button is configured with one or more pores connecting the first through hole with outside atmosphere.

The first seal, the second seal, the third seal and the fourth seal are each an annular elastic object surrounding an outer wall of the valve stem and arranged sequentially from top to bottom. The first seal is disposed height-wise between the button and the gas inlet and hermetically abuts an inner wall of the thick section of the valve housing. The second seal is disposed height-wise between the first seal and the horizontal section of the first through hole and forms a gap with the inner wall of the thick section of the valve housing. During operation of the button the second seal moves downward along with the valve stem to hermetically abut with either the intersection of the thick section and the thin section of the valve housing or an inner wall of the thin section. The third seal is disposed height-wise between the horizontal section of the first through hole and the fluid outlet and hermetically abuts the inner wall of the thin section of the valve housing. The fourth seal is disposed height-wise between the liquid inlet and the fluid outlet and hermetically abuts the inner wall of the thick section of the valve housing.

The valve stem includes a second through hole horizontally traversing the valve stem and disposed above the fourth seal and below a connection between the lower end of the first through hole and the valve core.

An endoscope in accordance with the present invention includes the above-described endoscopic fluid control valve.

As can be seen from the aforementioned prior art, embodiments of the present invention provides a number of advantages. The endoscopic fluid control valve needs only one outlet for liquid discharge and gas discharge so as to reduce the number of outlets on the control valve, thereby nullifying the need for the tee outside the control valve for combining the liquid outlet and gas outlet into the same pipeline. This results in a simpler structure and space saving in the endoscopic fluid control valve. Furthermore, through the joint action of the valve core, spring and seals, backflow of fluid may be prevented. As there is no need for a check valve along the pathway of fluids, it is easy to clean.

BRIEF DESCRIPTION OF THE DRAWINGS

In order to more clearly illustrate embodiments of the present invention or technical solutions of the prior art, a brief description of drawings associated with the embodiments of the present invention or technical solutions of the prior art is provided below. Obviously, drawings described below only pertain to some embodiments of the present invention. Those skilled in the art may obtain other drawings based on the following drawings under the premise of not spending any effort in innovation.

DETAILED DESCRIPTION OF PREFERRED EMBODIMENTS

The accompanying drawings and the following specific examples further illustrate the technical aspect of embodiments of the present invention. Apparently, the embodiments described below are merely part of the embodiments and not the entire embodiments. Other embodiments obtained by those skilled in the art, based on the embodiments of the present invention and under the premise of not spending any effort in innovation, are deemed to be within the protective scope of the present invention.

Embodiments of the present invention provide an endoscopic fluid control valve configured to clean the fluid control valve during the process of liquid feeding, which saves space inside the endoscope.

Figure 1:
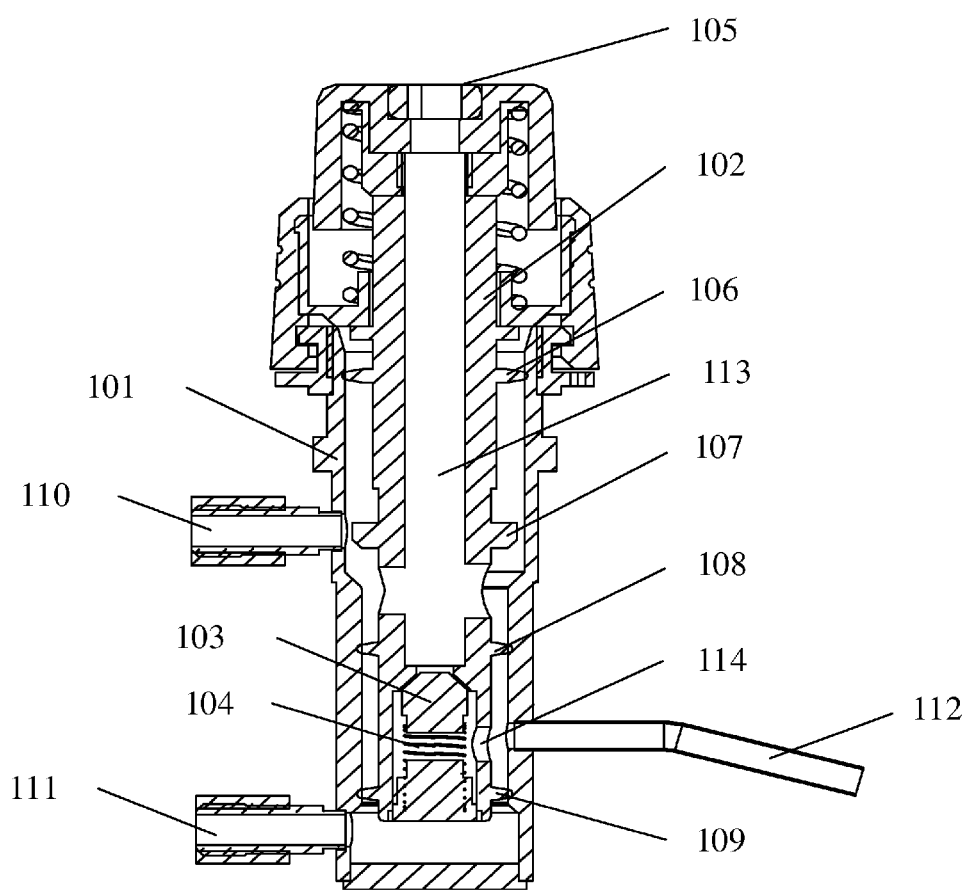
FIG. 1 is a cross-sectional view of an endoscopic fluid control valve in accordance with an embodiment of the present invention.

Referring to FIG. 1, an embodiment of a fluid control valve of an endoscope may include the following: valve housing 101, valve stem 102, vale body 103, elastic component 104, button 105, first seal 106, second seal 107, third seal 108, fourth seal 109, gas inlet 110, liquid inlet 111 and fluid outlet 112.

Valve housing 101 contains valve stem 102, valve core 103, elastic component 104, button 105, first seal 106, second seal 107 and third seal 108 therein. From top to bottom, the valve housing includes a thick section with larger inner diameter and a thin section with a smaller inner diameter, with gas inlet 110, fluid outlet 112 and liquid inlet 111 disposed on the valve housing 101 and arranged in the listed order from top to bottom. Gas inlet 110 is disposed on the thick section of the valve housing, and fluid outlet 112 and liquid inlet 111 are disposed on the thin section of valve housing 101.

Valve stem 102 has a through hole 113 therein. Through hole 113 includes an upper end, connected to button 105, and a lower end including a vertical section connected to an upper end of valve core 103 as well as a horizontal section traversing through valve stem 102. The horizontal section is disposed height-wise between gas inlet 110 and fluid outlet 112. Through hole 113 is configured to receive a gas that enters the valve stem. It is noteworthy that the through hole is a traversing hole that traverses through the valve stem.

Valve core 103 is contained within valve stem 102. A lower end of valve core 103 is connected to an upper end of elastic component 104. An upper end of valve core 103 detachably forms an airtight connection with the lower end of through hole 113. Elastic component 104 is contained within valve stem 102. An upper end of elastic component 104 is elastically connected to the lower end of valve core 103. A lower end of elastic component 104 is connected to a bottom end of valve stem 102.

Button 105 is disposed at a top portion of the endoscopic fluid control valve, and connected to the vertical section of through hole 113 of valve stem 102. Button 105 is configured with pore(s) connecting the through hole with outside atmosphere.

First seal 106, second seal 107, third seal 108 and fourth seal 109 are each an annular elastic object surrounding an outer wall of valve stem 102, and are arranged in the listed order from top to bottom. First seal 106 is disposed height-wise between button 105 and gas inlet 110, and hermetically abuts an inner wall of the thick section of valve housing 101. Second seal 107 is disposed height-wise between first seal 106 and the horizontal section of through hole 113, and forms a gap with the inner wall of the thick section of valve housing 101. The size of the gap is not limited and may be configured according to actual implementation. During operation of button 105, second seal 107 may move downward along with valve stem 102 to hermetically abut with either the intersection of the thick section and the thin section of valve housing 101 or an inner wall of the thin section. Third seal 108 is disposed height-wise between the horizontal section of through hole 113 and fluid outlet 112, and hermetically abuts the inner wall of the thin section of the valve housing. Fourth seal 109 is disposed height-wise between liquid inlet 111 and fluid outlet 112, and hermetically abuts the inner wall of the thick section of valve housing 101.

Valve stem 102 includes a through hole 114 horizontally traversing valve stem 102 and disposed above fourth seal 109 and below the connection between the lower end of through hole 113 and valve core 103.

In one embodiment, gas inlet 110, liquid inlet 111 and fluid outlet 112 may be disposed at any location on the circumference of the outer wall of valve stem 102 when the aforementioned height requirements are satisfied.

FIG. 1 is a structural diagram of an endoscopic fluid control valve under normal condition when a button is not pressed.

Figure 2:
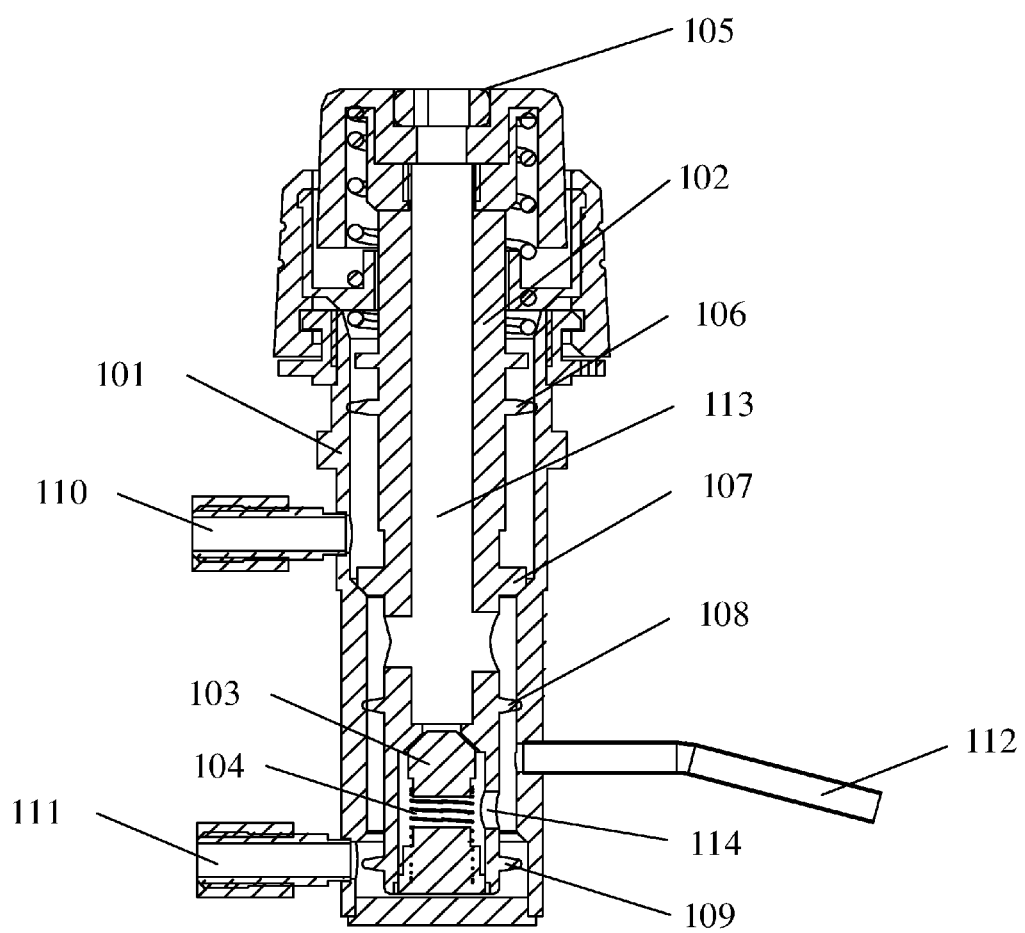
FIG. 2 is a cross-sectional view of the structure of the endoscopic fluid control valve of FIG. 1 when a button is pushed.

Detailed description of the operation of the endoscopic fluid control valve is provided below. Referring to FIG. 2, FIG. 2 is a structural diagram of the endoscopic fluid control valve when the button is pressed.

1. Working Process of Providing Gas into Body Cavity Through the Endoscopic Fluid Control Valve Gas inlet 110 of endoscopic fluid control valve is connected to a gas source, and liquid inlet 111 is connected to a liquid source. When button 105 is not pressed, fourth seal 109, which hermetically abuts valve housing 101, isolates an incoming liquid in a space below fourth seal 109.

When a gas enters through gas inlet 110 on the sidewall of the endoscopic valve housing 101, the incoming gas is confined to a gap between first seal 106 and third seal 108 because a gap exists between valve housing 101 and valve stem 102 and because first seal 106 and third seal 108 hermetically abut the inner wall of valve housing 101. The gas can only enter the vertical section of through hole 113 through a traversing opening of the horizontal section of through hole 113. As the lower end of through hole 113 is blocked by valve core 103, the gas is discharged upward through the pore(s) on the upper end of button 105.

Furthermore, when the pore(s) on the upper end of button 105 is/are blocked, first seal 106 and third seal 108 together limit the upward and downward flow of the gas, and confine the gas in a space between first seal 106 and third seal 108 and in the cavity of through hole 113 of valve stem 102. The pressure produced by the gas in the vertical section of through hole 113 pushes downward to open valve core 103 and correspondingly compresses elastic component 104. The gas is discharged from the lower end of through hole 113, traversing through a gap between valve core 103 and valve stem 102 as well as through hole 114 which horizontally traverses valve stem, to be discharged to a space between valve housing 101 and valve stem 102. As third seal 108 and fourth seal 109 hermetically abut the inner wall of the thin section of valve housing 102, the gas discharged to the space between valve housing 101 and valve stem 102 is confined to a gap between third seal 108 and fourth seal 109 to be discharged through fluid outlet 112, which is the only outlet of this gap, to enter into the body cavity through the pipeline of the insertion portion of the endoscope.

In one embodiment, each seal is an annular elastic object surrounding an outer wall of valve stem 102.

2. Working Process of Providing Liquid into Body Cavity Through the Endoscopic Fluid Control Valve When button 105 is pressed, valve stem 102 synchronously moves downward. Second seal 107 also synchronously moves downward to hermetically abut with either the intersection of the thick section and the thin section of valve housing 101 or with the inner wall of the thin section, thus isolating the gas in a space between first seal 106 and second seal 107. Meanwhile, fourth seal 109, which hermetically abuts valve housing 101, moves downward to below liquid inlet 111, and the liquid enters a space between third seal 108 and fourth seal 109. As the lower end of through hole 113 is blocked by valve core 103, the incoming liquid cannot enter into through hole 113 and can only be discharged through fluid outlet 112 of the fluid control valve. At the same time the rinsing of the endoscopic fluid control valve is complete.

From the above-described process of providing gas through the endoscopic fluid control valve it can be seen that, under normal condition with button 105 not pressed, when there is backflow of a fluid into the fluid control valve through fluid outlet 112, the fluid flowing into the fluid control valve is confined to the space between third seal 108 and fourth seal 109 and thus cannot enter gas inlet 110, valve stem through hole 113 or liquid inlet 111. This is because third seal 108 and valve core 103 isolate a path between gas inlet 110 and fluid outlet 112 as well as a path between valve stem through hole 113 and fluid outlet 112, and because fourth seal 109 isolates a path between liquid inlet 111 and fluid outlet 112. Moreover, when providing a liquid, the incoming liquid is also discharged from fluid outlet 112 by way of aforementioned spaces. Thus backflow of a fluid into such space(s) can be cleaned out during the process of providing the liquid.

It is noteworthy that, in one embodiment the valve housing may have, from top to bottom, a thick section with a larger inner diameter and a thin section with a smaller inner diameter, with an abrupt change in diameter at the intersection of the thick section and the thin section. Alternatively, from top to bottom, there may be a thick section with a larger inner diameter, a tapered section and a thin section with a smaller inner diameter. When button is pressed, second seal may fall on the intersection of the former structure, on the tapered section of the latter structure, or onto the thin section, so long as the gas inlet is hermetically isolated from the path below second seal.

In one embodiment, the endoscopic fluid control valve is configured with one outlet for the discharge of both liquid and gas so as to minimize the number of outlet on the valve body. This eliminates the need for a three-way tee for converging a liquid outlet and a gas outlet into a single pipeline outside the valve body, thereby simplifying the structure of the endoscopic fluid control valve and saving space. Additionally, due to the collective effect of valve core, spring and seals, backflow of bodily fluids, medical liquids, gases and water may be prevented without the need for a check valve along the path of fluid, and this makes it easy to clean.

Figure 3:
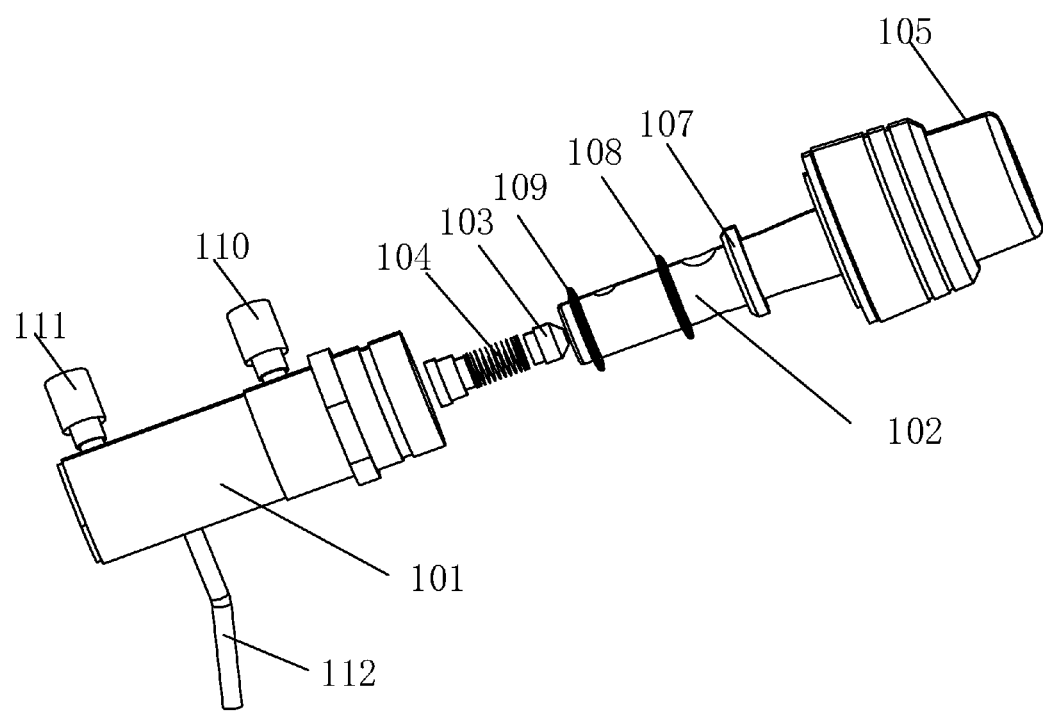
FIG. 3 is a perspective exploded view of the endoscopic fluid control valve of FIG. 1.

FIG. 3 is a structural diagram of an exploded view of the endoscopic fluid control valve of FIG. 1. As the components and functions thereof are the same as those shown in FIG. 1 and FIG. 2, in the interest of brevity a detailed description is not provided.

Detailed description of the operation of the endoscopic fluid control valve according to another embodiment is provided below with reference to FIG. 4.

Valve housing 201, valve stem 202, valve core 203, elastic component 204, button 205, first seal 206, second seal 207, third seal 208, fourth seal 209, gas inlet 210, liquid inlet 211, fluid outlet 212 are included.

Valve housing 201 contains valve stem 202, valve core 203, elastic component 204, first seal 206, second seal 207, third seal 208 and fourth seal 209 therein. From top to bottom, the valve housing includes a thick section with larger inner diameter and a thin section with a smaller inner diameter, with gas inlet 210, fluid outlet 212 and liquid inlet 211 disposed on the valve housing 201 and arranged in the listed order from top to bottom. Gas inlet 210 is disposed on the thick section of the valve housing, and fluid outlet 212 and liquid inlet 211 are disposed on the thin section of valve housing 201.

Valve stem 202 has a through hole 213 therein. Through hole 213 includes an upper end, connected to button 205, and a lower end including a vertical section connected to an upper end of valve core 203 as well as a horizontal section traversing through valve stem 202. The horizontal section is disposed height-wise between gas inlet 210 and fluid outlet 212. Through hole 213 is configured to receive a gas that enters the valve stem. It is noteworthy that the through hole is a traversing hole that traverses through the valve stem.

Valve core 203 is contained within valve stem 202. A lower end of valve core 203 is connected to an upper end of elastic component 204. An upper end of valve core 203 detachably forms an airtight connection with the lower end of through hole 213. Elastic component 204 is contained within valve stem 202. An upper end of elastic component 204 is elastically connected to the lower end of valve core 203. A lower end of elastic component 204 is connected to a bottom end of valve stem 202.

Button 205 is disposed at a top portion of the endoscopic fluid control valve, and connected to the vertical section of through hole 213 of valve stem 202. Button 205 is configured with pore(s) connecting the through hole with outside atmosphere. Button 205 can move up and down, depending on a pressure exerted thereon, and synchronously move the valve stem up and down.

First seal 206, second seal 207, third seal 208 and fourth seal 209 are each an annular elastic object surrounding an outer wall of valve stem 202, and are arranged in the listed order from top to bottom. First seal 206 is disposed height-wise between button 205 and gas inlet 210, and hermetically abuts an inner wall of the thick section of valve housing 201. Second seal 207 is disposed height-wise between first seal 206 and the horizontal section of through hole 213, and forms a gap with the inner wall of the thick section of valve housing 201. The size of the gap is not limited and may be configured according to actual implementation. During operation of button 205, second seal 207 may move downward along with valve stem 202 to hermetically abut with either the intersection of the thick section and the thin section of valve housing 201 or an inner wall of the thin section. Third seal 208 is disposed height-wise between the horizontal section of through hole 213 and fluid outlet 212, and hermetically abuts the inner wall of the thin section of the valve housing. Fourth seal 209 is disposed height-wise between liquid inlet 211 and fluid outlet 212, and hermetically abuts the inner wall of the thick section of valve housing 201.

Valve stem 202 includes a through hole 214 horizontally traversing valve stem 202 and disposed above fourth seal 209 and below the connection between the lower end of through hole 213 and valve core 203.

In one embodiment, gas inlet 210, liquid inlet 211 and fluid outlet 212 may be disposed at any location on the circumference of the outer wall of valve stem 202 when the aforementioned height requirements are satisfied.

Further, the endoscopic fluid control valve may include at least a guide ring.

The guide ring is an annular object surrounding an outer wall of the valve stem, and is configured to ensure smooth movement of the valve stem when the valve stem slides up and down along the inner wall of the endoscopic fluid control valve.

Figure 4:
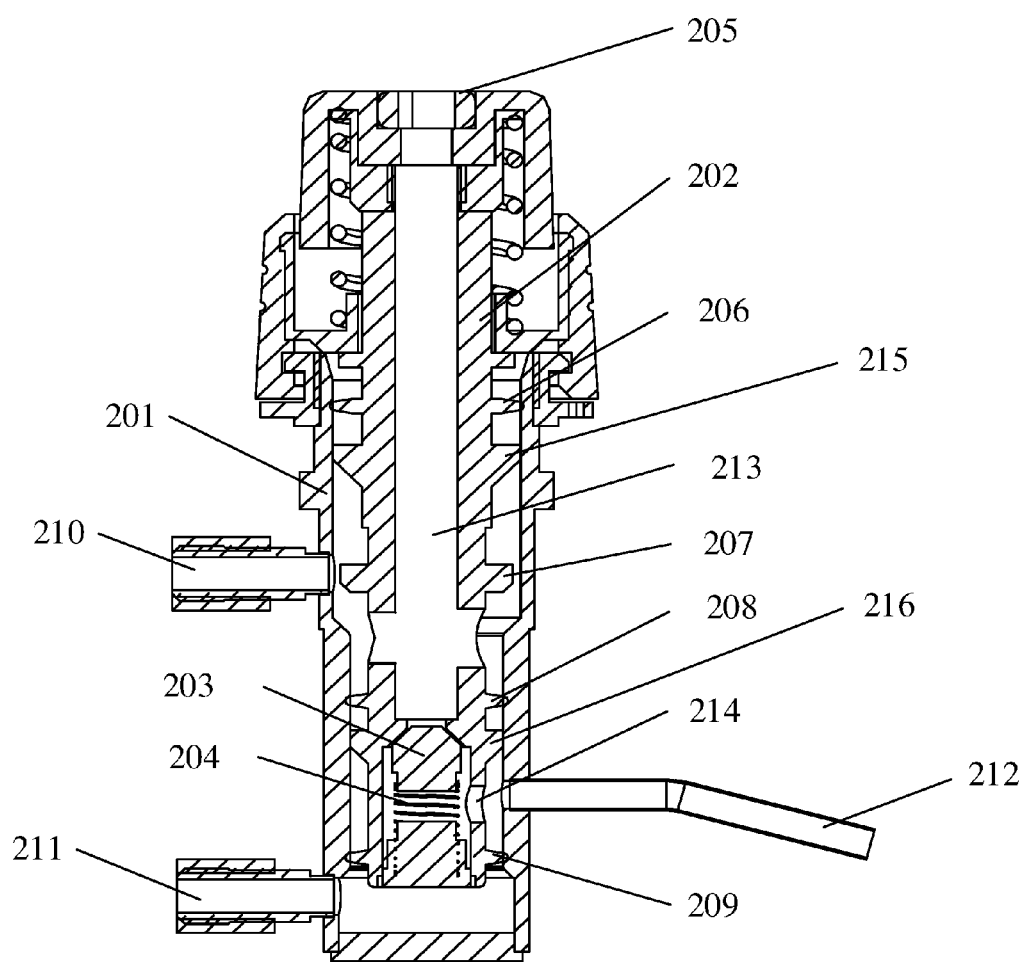
FIG. 4 is a cross-sectional view of an endoscopic fluid control valve in accordance with another embodiment of the present invention.

Referring to FIG. 4, which shows two guide rings, namely first guide ring 215 and second guide ring 216, with first guide ring 215 and second guide ring 216 disposed on valve stem 202 in the listed order from top to bottom.

A small preset gap exists between First guide ring 215, second guide ring 216 and the inner wall of the valve housing 201. The size of the gap is preset based on the actual need and is not specifically limited. The gap allows the valve stem to smoothly slide up and down without deviation with respect to the inner wall of the valve housing 201.

Figure 5:
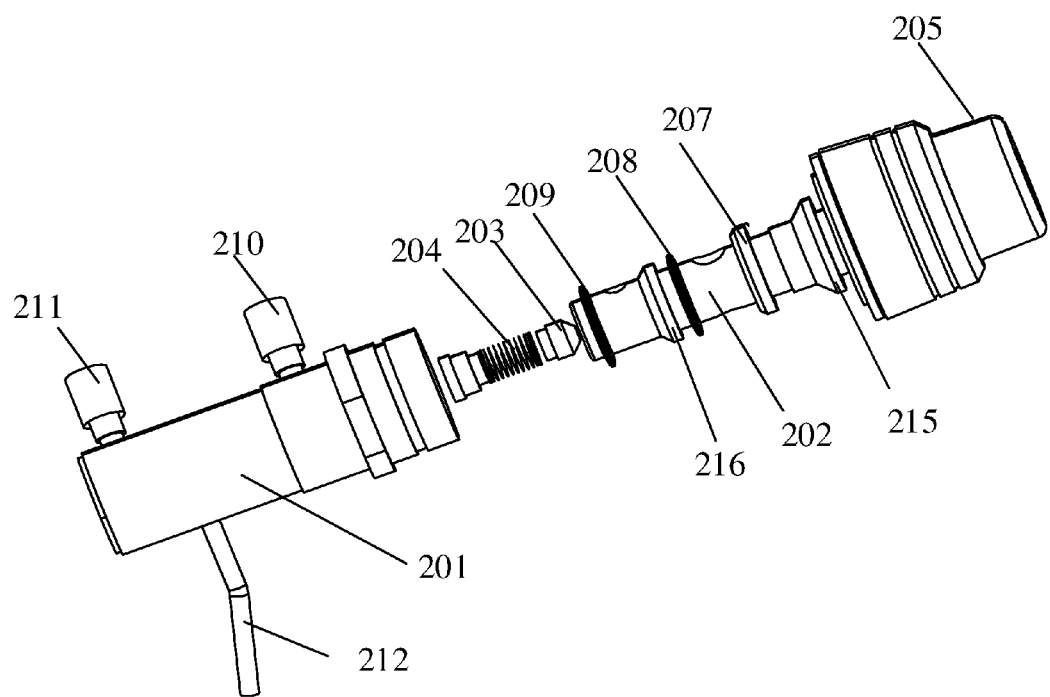
FIG. 5 is a perspective exploded view of the endoscopic fluid control valve of FIG. 4.

FIG. 5 is a structural diagram of an exploded view of the endoscopic fluid control valve of FIG. 4. As the components and functions thereof are the same as those shown in FIG. 4, in the interest of brevity a detailed description is not provided.

In the aforementioned embodiments, first seal, second seal, third seal, fourth seal and valve stem may be formed by press molding for a high degree of integration and ease of manufacturing.

First guide ring and second guide ring are made of a polyformaldehyde (POM) material, and can reduce friction between inner walls of the valve body to achieve smoothness. First guide ring, second guide ring and valve stem may be formed by injection molding for a high degree of integration, and this improves the stability of the guide rings to better act as a guide.

Valve stem may be made of stainless steel, which is less susceptible to liquid corrosion so as to prolong the life of equipment.

In one embodiment, the specific working process of the endoscopic fluid control valve for providing gas and liquid may be referred to the embodiments pertaining to FIG. 1 and FIG. 2, and thus in the interest of brevity a detailed description thereof is not provided.

In one embodiment, the endoscopic fluid control valve is configured with one outlet for the discharge of both liquid and gas so as to minimize the number of outlet on the valve body. This eliminates the need for a three-way tee for converging a liquid outlet and a gas outlet into a single pipeline outside the valve body, thereby simplifying the structure of the endoscopic fluid control valve and saving space. Additionally, due to the collective effect of valve core, spring and seals, backflow of bodily fluids, medical liquids, gases and water may be prevented without the need for a check valve along the path of fluid, and this makes it easy to clean. The use of guide rings allows the valve stem to smoothly slide up and down without deviation with respect to the inner wall of the valve body. First seal, second seal, third seal, fourth seal and valve stem may be formed by press molding for a high degree of integration and ease of manufacturing. First guide ring, second guide ring and valve stem may be formed by injection molding for a high degree of integration, and this improves the stability of the guide rings to better act as a guide.

The present invention also provides an endoscope that utilizes the above-described endoscopic fluid control valve. The working principle of the endoscope and improvements in its structure compared to the prior art have been introduced above with respect to the endoscopic fluid control valve, and thus in the interest of brevity a detailed description thereof is not provided.

Detailed descriptions of an endoscopic fluid control valve and an endoscope using the same in accordance with the present invention are provided above. In view of the above, those skilled in the art may make modifications in actual implementations and applications based on the concept of the present invention and their equivalents. The content of the specification is not to be deemed as limiting the scope of the present invention.

What is claimed is:

1. An endoscopic fluid control valve, comprising:
   a valve housing;
   a valve stem;
   a valve core;
   an elastic component;

a button;
a first seal;
a second seal;
a third seal;
a fourth seal;
a gas inlet configured to allow a gas to flow into the endoscopic fluid control valve;
a liquid inlet configured to allow a liquid to flow into the endoscopic fluid control valve; and
a gas and liquid outlet configured to allow the gas and the liquid to be discharged from the endoscopic fluid control valve,
wherein the valve housing contains the valve stem, the valve core, the elastic component, the first seal, the second seal, the third seal and the fourth seal therein,
wherein the valve housing includes following parts arranged in an order as listed from top to bottom: a thick section with a larger diameter and a thin section with a smaller diameter,
wherein the gas inlet, the gas and liquid outlet and the liquid inlet are arranged on the valve housing in a sequential order from top to bottom, with the gas inlet disposed on the thick section of the valve housing and with the gas and liquid outlet and the liquid inlet disposed on the thin section of the valve housing,
wherein the valve stem comprises a first through hole which has an upper end and a lower end, wherein the upper end of the first through hole is connected to the button, wherein the lower end of the first through hole includes a vertical section connected to an upper end of the valve core,
wherein the lower end of the first through hole also includes a horizontal section horizontally traversing through the valve stem, and wherein the horizontal section is disposed height-wise below the gas inlet and above the gas and liquid outlet,
wherein the valve core is contained within the valve stem and comprises a lower end and the upper end, wherein the lower end of the valve core is connected to an upper end of the elastic component, wherein the upper end of the valve core detachably forms an airtight connection with the lower end of the first through hole,
wherein the elastic component is contained within the valve stem and comprises the upper end and a lower end, wherein the upper end of the elastic component is elastically connected to the lower end of the valve core, and wherein the lower end of the elastic component is connected to a bottom end of the valve stem,
wherein the button is disposed at a top portion of the endoscopic fluid control valve and is connected to the vertical section of the first through hole, and wherein the button is configured with one or more pores connecting the first through hole with outside atmosphere,
wherein the first seal, the second seal, the third seal and the fourth seal are each an annular elastic object surrounding an outer wall of the valve stem and arranged sequentially from top to bottom, wherein the first seal is disposed height-wise between the button and the gas inlet and hermetically abuts an inner wall of the thick section of the valve housing, wherein the second seal is disposed height-wise between the first seal and the horizontal section of the first through hole and forms a gap with the inner wall of the thick section of the valve housing, wherein the third seal is disposed height-wise between the horizontal section of the first through hole and the gas and liquid outlet and hermetically abuts the inner wall of the thin section of the valve housing, and wherein the fourth seal is disposed height-wise between the liquid inlet and the gas and liquid outlet and hermetically abuts the inner wall of the thick section of the valve housing,
wherein the valve stem includes a second through hole horizontally traversing the valve stem and disposed between the third seal and the fourth seal and also below a connection between the lower end of the first through hole and the valve core,
wherein, when the button is not pressed, the gas flowing into the endoscopic fluid control valve through the gas inlet is confined in a space between the first seal and the third seal and also in a cavity of the first through hole of the valve stem such that a pressure of the gas pushes the valve core downward to compress the elastic component to push the valve core downward to allow the gas to be discharged through the gas and liquid outlet by flowing through a gap between the valve core and the valve stem, the second through hole, and a space between the third seal and the fourth seal, and
wherein, when the button is pressed, the second seal synchronously moves downward along with the valve stem to hermetically abut with either an inner wall of the thin section or with the intersection of the thick section and the thin section of the valve housing such that: (1) the gas is confined in the gap between the first seal and the second seal, (2) the fourth seal, which hermetically abuts the valve housing, moves downward to a point below the liquid inlet, and (3) the liquid flowing into the endoscopic fluid control valve through the liquid inlet is confined in a space between the third seal and the fourth seal and is discharged through the gas and liquid outlet, while the lower end of the first through hole is blocked by the valve core to prevent the liquid from entering into the first through hole.

2. The endoscopic fluid control valve of claim 1, wherein the first seal, the second seal, the third seal, the fourth seal and the valve stem are integrated by press molding or fixed together by adhesion.

3. The endoscopic fluid control valve of claim 1, further comprising:
at least one guide ring,
wherein the at least one guide ring comprises an annular object surrounding an outer wall of the valve stem and is configured to ensure smooth movement of the valve stem when the valve stem slides up and down along an inner wall of the endoscopic fluid control valve.

4. The endoscopic fluid control valve of claim 3, wherein the at least one guide ring and the valve stem are integrally formed by injection molding.

5. The endoscopic fluid control valve of claim 3, wherein the at least one guide ring is made of polyformaldehyde.

6. The endoscopic fluid control valve of claim 1, wherein the valve stem is made of stainless steel.

7. The endoscopic fluid control valve of claim 1, wherein the valve core seals the lower end of the first through hole.

8. The endoscopic fluid control valve of claim 1, wherein the gap separates the second seal from the inner wall of the thick section of the valve housing when the button is not pressed.

9. An endoscope, comprising:
an endoscopic fluid control valve comprising:
a valve housing;
a valve stem;
a valve core;
an elastic component;
a button;

a first seal;
a second seal;
a third seal;
a fourth seal;
a gas inlet configured to allow a gas to flow into the endoscopic fluid control valve;
a liquid inlet configured to allow a liquid to flow into the endoscopic fluid control valve; and
a gas and liquid outlet configured to allow the gas and the liquid to be discharged from the endoscopic fluid control valve,
wherein the valve housing contains the valve stem, the valve core, the elastic component, the first seal, the second seal, the third seal and the fourth seal therein,
wherein the valve housing includes following parts arranged in an order as listed from top to bottom: a thick section with a larger diameter and a thin section with a smaller diameter,
wherein the gas inlet, the gas and liquid outlet and the liquid inlet are arranged on the valve housing in a sequential order from top to bottom, with the gas inlet disposed on the thick section of the valve housing and with the gas and liquid outlet and the liquid inlet disposed on the thin section of the valve housing,
wherein the valve stem comprises a first through hole which has an upper end and a lower end, wherein the upper end of the first through hole is connected to the button, wherein the lower end of the first through hole includes a vertical section connected to an upper end of the valve core, wherein the lower end of the first through hole also includes a horizontal section horizontally traversing through the valve stem, and wherein the horizontal section is disposed height-wise below the gas inlet and above the gas and liquid outlet,
wherein the valve core is contained within the valve stem and comprises a lower end and the upper end, wherein the lower end of the valve core is connected to an upper end of the elastic component, wherein the upper end of the valve core detachably forms an airtight connection with the lower end of the first through hole,
wherein the elastic component is contained within the valve stem and comprises the upper end and a lower end, wherein the upper end of the elastic component is elastically connected to the lower end of the valve core, and wherein the lower end of the elastic component is connected to a bottom end of the valve stem,
wherein the button is disposed at a top portion of the endoscopic fluid control valve and is connected to the vertical section of the first through hole, and wherein the button is configured with one or more pores connecting the first through hole with outside atmosphere,
wherein the first seal, the second seal, the third seal and the fourth seal are each an annular elastic object surrounding an outer wall of the valve stem and arranged sequentially from top to bottom, wherein the first seal is disposed height-wise between the button and the gas inlet and hermetically abuts an inner wall of the thick section of the valve housing, wherein the second seal is disposed height-wise between the first seal and the horizontal section of the first through hole and forms a gap with the inner wall of the thick section of the valve housing, wherein the third seal is disposed height-wise between the horizontal section of the first through hole and the gas and liquid outlet and hermetically abuts the inner wall of the thin section of the valve housing, and wherein the fourth seal is disposed height-wise between the liquid inlet and the gas and liquid outlet and hermetically abuts the inner wall of the thick section of the valve housing,
wherein the valve stem includes a second through hole horizontally traversing the valve stem and disposed between the third seal and the fourth seal and also below a connection between the lower end of the first through hole and the valve core,
wherein, when the button is not pressed, the gas flowing into the endoscopic fluid control valve through the gas inlet is confined in a space between the first seal and the third seal and also in a cavity of the first through hole of the valve stem such that a pressure of the gas pushes the valve core downward to compress the elastic component to push the valve core downward to allow the gas to be discharged through the gas and liquid outlet by flowing through a gap between the valve core and the valve stem, the second through hole, and a space between the third seal and the fourth seal, and
wherein, when the button is pressed, the second seal synchronously moves downward along with the valve stem to hermetically abut with either an inner wall of the thin section or with the intersection of the thick section and the thin section of the valve housing such that: (1) the gas is confined in the gap between the first seal and the second seal, (2) the fourth seal, which hermetically abuts the valve housing, moves downward to a point below the liquid inlet, and (3) the liquid flowing into the endoscopic fluid control valve through the liquid inlet is confined in a space between the third seal and the fourth seal and is discharged through the gas and liquid outlet.

10. The endoscope of claim 9, wherein the first seal, the second seal, the third seal, the fourth seal and the valve stem are integrated by press molding or fixed together by adhesion.

11. The endoscope of claim 9, further comprising:
at least one guide ring,
wherein the at least one guide ring comprises an annular object surrounding an outer wall of the valve stem and is configured to ensure smooth movement of the valve stem when the valve stem slides up and down along an inner wall of the endoscopic fluid control valve.

12. The endoscope of claim 9, wherein the at least one guide ring and the valve stem are integrally formed by injection molding.

13. The endoscope of claim 9, wherein the at least one guide ring is made of polyformaldehyde.

14. The endoscope of claim 9, wherein the valve stem is made of stainless steel.

15. The endoscopic fluid control valve of claim 9, wherein the valve core seals the lower end of the first through hole.

16. The endoscopic fluid control valve of claim 9, wherein the gap separates the second seal from the inner wall of the thick section of the valve housing when the button is not pressed.

* * * * *